(12) United States Patent
Dreyfuss et al.

(10) Patent No.: US 8,506,573 B2
(45) Date of Patent: Aug. 13, 2013

(54) OFFSET DRILL GUIDE AND ARTHROSCOPIC METHOD

(75) Inventors: Peter J. Dreyfuss, Naples, FL (US); Albert F. Haas, Mobile, AL (US)

(73) Assignee: Arthrex, Inc., Naples, FL (US)

( * ) Notice: Subject to any disclaimer, the term of this patent is extended or adjusted under 35 U.S.C. 154(b) by 1501 days.

(21) Appl. No.: 11/735,814

(22) Filed: Apr. 16, 2007

(65) Prior Publication Data
US 2007/0288031 A1 Dec. 13, 2007

Related U.S. Application Data

(62) Division of application No. 10/642,688, filed on Aug. 19, 2003, now Pat. No. 7,204,839.

(60) Provisional application No. 60/407,690, filed on Sep. 4, 2002.

(51) Int. Cl.
*A61B 17/58* (2006.01)

(52) U.S. Cl.
USPC .......................................................... 606/96

(58) Field of Classification Search
USPC ................................................ 606/96–98
See application file for complete search history.

(56) References Cited

U.S. PATENT DOCUMENTS

| | | | |
|---|---|---|---|
| 4,719,907 A | 1/1988 | Banko et al. | |
| 5,520,693 A * | 5/1996 | McGuire et al. | 606/86 R |
| 5,624,446 A * | 4/1997 | Harryman, II | 606/96 |
| 5,681,333 A * | 10/1997 | Burkhart et al. | 606/148 |
| 5,690,677 A | 11/1997 | Schmieding et al. | |
| 5,814,073 A | 9/1998 | Bonutti | |
| 6,096,044 A * | 8/2000 | Boyd et al. | 606/96 |
| 6,273,892 B1 * | 8/2001 | Orbay et al. | 606/96 |
| 6,322,565 B1 * | 11/2001 | Garner et al. | 606/96 |

* cited by examiner

*Primary Examiner* — Kevin T Truong
*Assistant Examiner* — Michael Araj
(74) *Attorney, Agent, or Firm* — Dickstein Shapiro LLP

(57) ABSTRACT

A cannulated offset drill guide and surgical methods for repairing Bankart lesions. The cannulated offset drill guide comprising a shaft which is offset from the guide center line by about 1 to 3 mm, more preferably of about 1.5 mm. The cannulated offset drill guide is provided at its proximal end with a concave clear tip which allows a surgeon to visualize the drill and the insertion of an anchoring device, for example a suture anchor. The concave clear tip has beveled, smooth edges to prevent damage to adjacent bone and tissue, and to avoid damage to the rubber dam of the cannula through which the offset drill guide is inserted. The configuration of the concave clear tip is designed to engage and match the generally convex-curve articulating face of the glenoid, and to precisely aligning the offset drill guide with the glenoid face. The clear tip may also be employed in a standard drill guide having a shaft which is not offset from the center line of the guide.

13 Claims, 6 Drawing Sheets

US 8,506,573 B2

OFFSET DRILL GUIDE AND ARTHROSCOPIC METHOD

This application is a divisional of Ser. No. 10/642,688, filed Sep. 4, 2002, now U.S. Pat. No. 7,204,839, which claims the benefit of U.S. Provisional Application Ser. No. 60/407,690, filed Sep. 4, 2002, the entire disclosure of which is incorporated by reference herein.

FIELD OF THE INVENTION

The present invention relates to the field of arthroscopic surgery and, more particularly, to an offset drill guide for surgical repairs such as Bankart repair.

BACKGROUND OF THE INVENTION

A Bankart lesion is a tear in the shoulder and typically entails the instability of the shoulder joint which occurs subsequent to a shoulder dislocation. This instability is commonly the result of a tearing of the joint capsule and its glenoid labrum, a fibrocartilaginous structure, from the anterior aspect of the glenoid. One surgical intervention for correcting the instability associated with a Bankart lesion is reattachment of the torn capsule and glenoid labrum to bone, on the anterior facet of the glenoid.

An arthroscopic Bankart repair typically involves: (i) embedding a suture anchor in a bony bed; (ii) passing a suture, which is attached to the embedded suture anchor, through the soft tissue which is to be reattached to the bony bed; and (iii) tying the soft tissue to the suture anchor, thus coapting the torn tissue to the bony bed.

Guiding small suture anchors while accurately positioning repair tissue an driving the suture anchors into bone can be excessively complex. Particularly, in an arthroscopic Bankart repair, inserting suture anchors into the glenoid rim is technically demanding, rendering the procedure extremely difficult.

In a Bankart intervention, the surgeon must visually assess the axis of the glenoid to gain access to it and see the glenoid for placement of an anchoring device, for example a bioabsorbable suture anchor. However, the deltoid muscle, tendons and other tissue obscure the glenoid neck and it is undesirable to disturb this region. Therefore, the surgeon has no visualization of the anatomy behind the face of the glenoid, particularly with regard to the thickness and orientation of the glenoid neck which does not correspond with the axis of the glenoid. Thus, there is always a risk that the anchoring device will either impinge on the sloping back wall of the neck, which will lead to unsatisfactory placement of the implant against the glenoid face, or will penetrate the cortical bone which may result in bone fracture or interference with or damage to soft tissue.

In addition, the anatomy of the glenoid itself provides very little bone into which an anchoring device can be placed. The articulating surface of the joint consists of a shallow dished cartilaginous area bonded by soft tissue of the rotator cuff which stabilizes the humeral head against the glenoid. While the lateral aspect of the glenoid presents a broad surface for articulation, its margins taper rapidly medially to form a narrow neck of about 10 to 15 mm thickness from which emerge the coracoid (superiorly) and acromial (posteriorly) processes. The thinning of the glenoid progresses into the scapula where the thickness may be as little as 2 mm to 3 mm, although there is a broader spine running along the inferior margin of the scapula. In addition, disease or degeneration can severely restrict the size of the glenoid, rendering implant placement even more problematic. For example, when an anchoring device is inserted into the articulating surface of the glenoid adjacent the damaged labrum to allow labral repair, the labrum tends to pull off the narrow and vertical articulating surface of the glenoid.

Accordingly, there is a need for an arthroscopic instrument and method that mobilizes the glenoid and the adjacent ligaments and labrum, and provides a secure platform for inserting an anchoring device, such as a suture anchor, into the glenoid to allow labral repair at a predefined specific position. There is also a need for a drill guide that is capable of limiting or controlling the depth of insertion of a drill in the bone such that a bore is formed only slightly into the glenoid face. The need also exists for a method of conducting a Bankart repair with a drill guide to a shallow predetermined depth, while minimizing the amount of bone removed and the force applied to the bone to allow the labrum to be attached as high as possible on the glenoid face relative to the glenoid articulating surface.

BRIEF SUMMARY OF THE INVENTION

The present invention overcomes the disadvantages of the prior art and fulfills the need noted above by providing a cannulated offset drill guide comprising a shaft which is offset from the guide center line, and a method of conducting a surgical repair, such as a Bankart repair, employing the cannulated offset drill of the present invention.

In one aspect, the invention provides a cannulated offset drill guide comprising a shaft which is offset from the guide center line by about 1 to 3 mm, more preferably of about 1.5 mm. The cannulated offset drill guide is provided at its proximal end with a concave clear tip which allows a surgeon to visualize the drill and the insertion of an anchoring device, for example a suture anchor. The concave clear tip has beveled, smooth edges to prevent damage to adjacent bone and tissue, and to avoid damage to the rubber dam of the cannula through which the offset drill guide is inserted. The configuration of the concave clear tip is designed to engage and match the generally convex-curve articulating face of the glenoid. By precisely aligning the offset drill guide with the glenoid face in this way, the offset shaft allows the placement of a pilot or blind hole for an anchoring device, for example a suture anchor, on the glenoid face at a precise location and with minimal amount of bone removed.

In another aspect, the invention provides a method for repairing a Bankart lesion and securing the glenoid labrum to the glenoid at the anatomically correct location by employing a cannulated offset drill guide. The offset drill guide comprises a shaft which is offset from the guide center line by about 1 to 3 mm, more preferably of about 1.5 mm. At least two anterior portals are provided anterior to the surgical repair site to access the Bankart lesion. A posterior portal is opened for a generally forward-directed cannula at a location just inferior to the postero-lateral corner of the acromion to provides access to the affected area by the offset drill guide of the present invention. Once any adhesions between the glenoid labrum and the glenoid have removed, the offset drill guide, with an obturator in its shaft, is inserted through the cannula into the surgical site, approaching the area to be repaired with its concave clear tip.

Once the labrum has been penetrated, the obturator is retrograded and the offset drill guide is seated at approximately 5:00 or 5:30 position relative to the right shoulder, for example. The offset drill guide is placed so that its concave clear tip is positioned with its concave-shaped surface in direct and precise alignment with the convex-shaped bony surface of the glenoid rim. The concave surface of the offset drill guide through which its offset shaft opens is placed against and engages the convex rim of the glenoid, helping to stabilize the drill guide.

Once the offset drill guide has been positioned in direct and precise alignment with the glenoid rim, a drill pin is inserted through offset drill guide and a drill hole is created to the drill stop and into the glenoid face. The drill pin is then removed and an implant, such as Arthrex Bio-Suture Tak 3 mm implant, is inserted through the drill guide to a laser line matching the back of the drill guide. Sutures are brought out through the superior cannula and knots may be subsequently formed in a conventional manner. The offset drill guide and suture guide may be reinserted to repeat the procedure at another location along the lesion.

Other features and advantages of the present invention will become apparent from the following description of the invention which refers to the accompanying drawings.

DETAILED DESCRIPTION OF THE INVENTION

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a cannulated offset drill guide for repairing a Bankart lesion by securing the fibrocartilage periphery (the glenoid labrum) to the glenoid at the anatomically correct location. As described in more detail below, the cannulated offset drill guide of the present invention comprises a shaft which is offset from the guide center line by about 1 to 3 mm, more preferably of about 1.5 mm. The cannulated offset drill guide is provided at its proximal end with a concave clear tip which allows a surgeon to visualize the drill and the insertion of an anchoring device, for example, a suture anchor. The concave clear tip has smooth edges to prevent damage to adjacent bone and tissue and to prevent damage to the rubber dam attached to the cannula through which the offset drill guide is inserted.

The configuration of the concave clear tip is designed to engage and match the generally convex-curve articulating face of the glenoid. By precisely aligning the offset drill guide with the glenoid facet in this way, the offset shaft allows the placement of a pilot or blind hole for an anchoring device, for example an absorbable suture anchor, on the glenoid face at a precise location and with minimal amount of bone removed.

Figure 1:
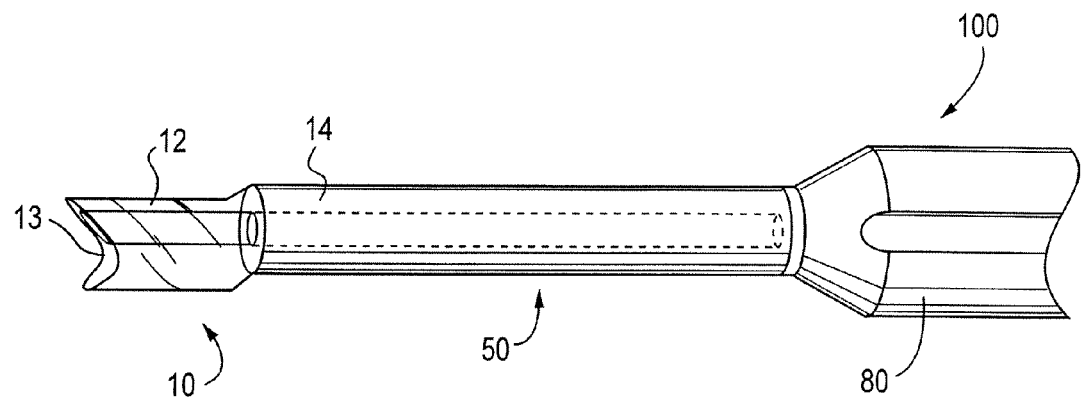
FIG. 1 illustrates an offset drill guide according to the present invention.
Figure 2:
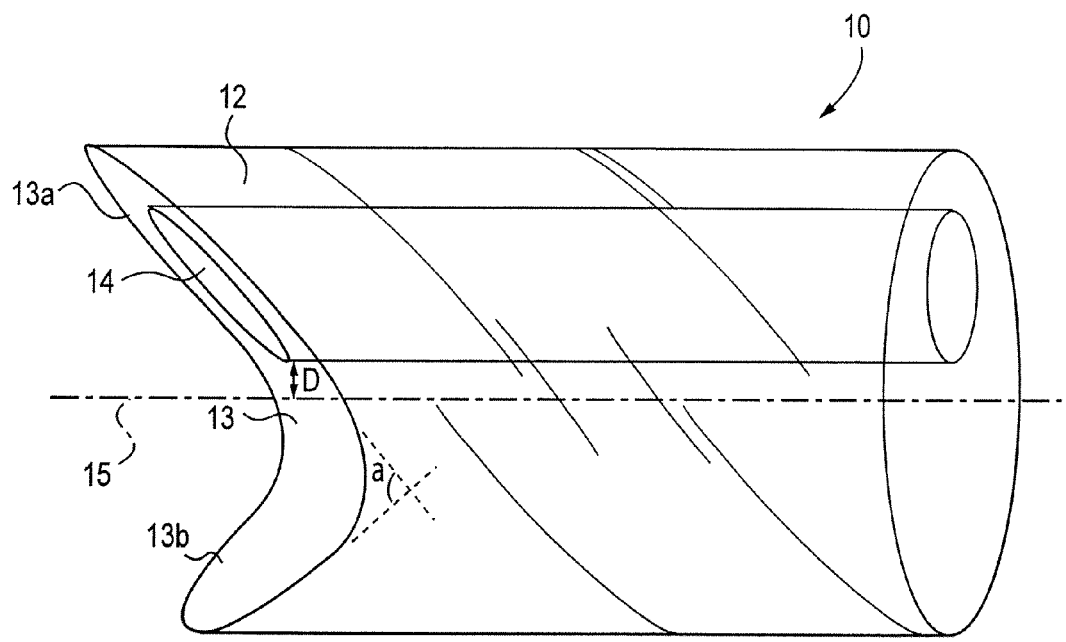
FIG. 2 illustrates the tip of the offset drill guide of FIG. 1.

Referring now to the drawings, where like elements are designated by like reference numerals, FIGS. 1-2 illustrate an offset cannulated drill guide 100 according to the present invention. The cannulated offset drill guide 100 comprises a cannulated elongated body 50 secured to a handle 80. The offset cannulated drill guide 100 also comprises a cannula 14 that extends through shaft 12 and handle 80 for receiving a suture anchor driver, as described in more detail below. An offset guide tip 10 is formed on the distal end of the elongated body 50. The offset guide tip 10 is clear and is provided with a concave distal surface 13.

As discussed further below, the clear tip 10 of the cannulated offset drill guide 100 allows the surgeon to visualize the drill and the insertion of the suture anchor through the drill guide. This important feature of the invention, i.e., a drill guide with a clear tip, may be employed in a co-linear (i.e., non-offset) drill guide, as described in more detail below.

FIG. 2 illustrates an enlarged end view of the offset guide tip 10 and of the concave surface 13. As illustrated in FIG. 2, the concave distal surface 13 has two curved, inclined surfaces 13a, 13b which form an angle "α" relative to center line 15 of the cannulated offset drill guide 100. Preferably, the angle "α" is greater than 90 degrees, more preferably of about 110 to about 130 degrees. As also shown in FIG. 2, and as a result of the shaft being offset from the central line 15, the inclined surfaces 13a and 13b have different areas. The inclined surface with the offset shaft (inclined surface 13a of FIG. 2) is larger than the adjacent inclined surface (inclined surface 13b of FIG. 2).

The concave configuration of the guide tip 10 engages and accurately matches the generally convex-curve articulating face of the glenoid rim. As described below, by precisely aligning the offset drill guide 100 with the glenoid face, the offset shaft 12 allows the placement of a pilot hole for an anchoring device, for example a suture anchor, on the glenoid face at a precise location and with minimal amount of bone removed. In addition, the concave shape of the offset drill guide tip 10 aligned with the glenoid face allows a surgeon to have more control over the offset drill guide 100. More importantly, the concave shape of the offset drill guide tip 10 aligned with the glenoid face avoids "skiving" of the drill guide over the articular surface or along the glenoid neck, as well as the placement of the drill hole too close to the medial line of the glenoid, which typically occur when a conventional, non-offset drill guide is employed.

FIG. 2 also illustrates cannula 14 of the shaft 12 offset from the longitudinal guide center line 15 by a predetermined distance "D" of about 1 to 3 mm, more preferably of about 1.5 mm. Cannula 14 also extends obliquely relative to the guide center line 15.

A preferred method of employing the offset cannulated drill guide 100 for installing suture anchors in accordance with the present invention is described below with reference to FIGS. 3-8.

Figure 3:
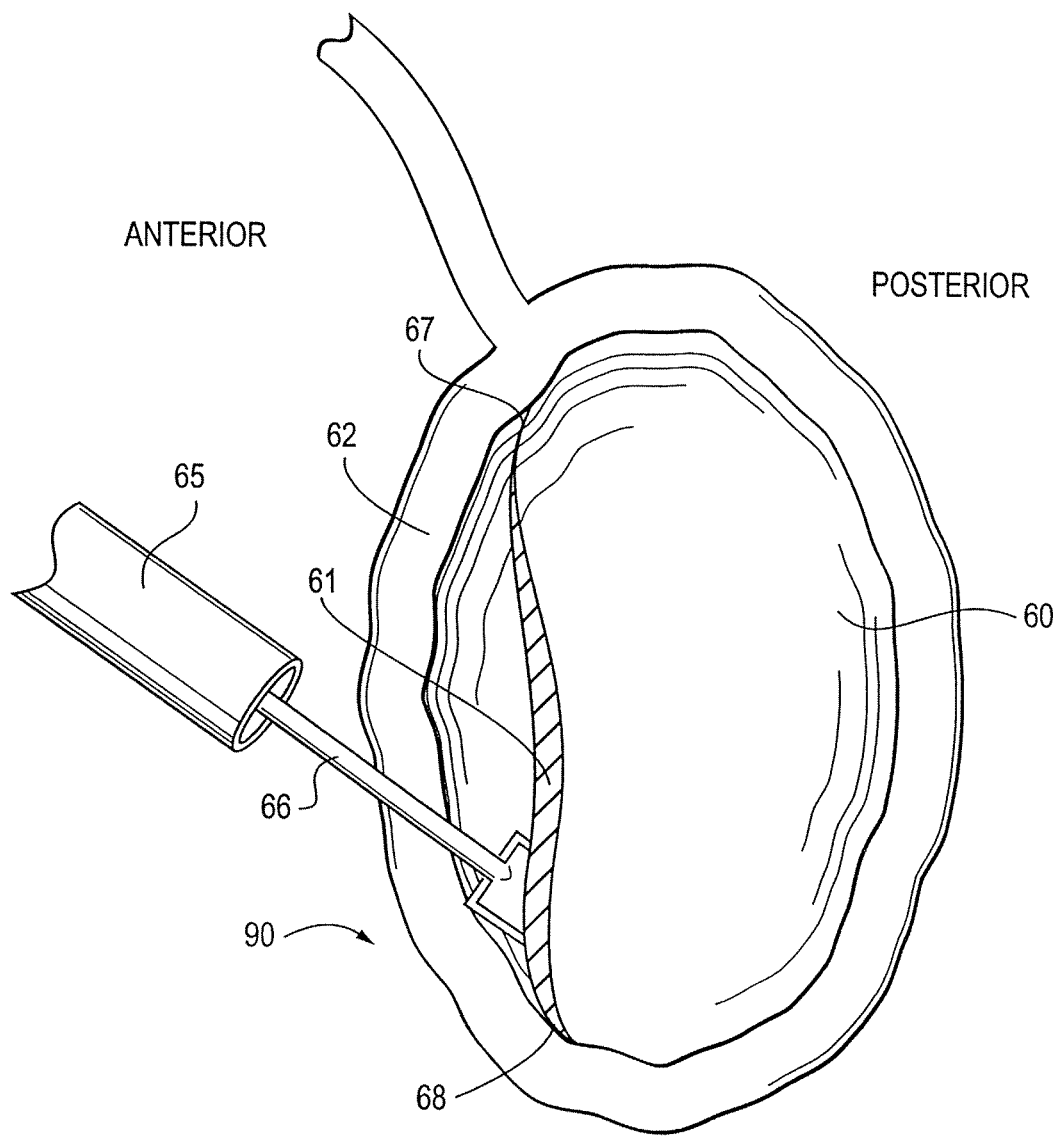
FIG. 3 illustrates a method step of preparing a surgical site for anatomic repair according to the present invention.

FIG. 3 illustrates schematically the anatomy in shoulder area 90 of a Bankart lesion repairable by employing the offset cannulated drill guide 100 of the present invention. For simplicity, the scapular side of the shoulder joint, the humerus and other adjacent tissue are not illustrated. Shallow glenoid cavity 60 is normally encircled by the articular capsule of connective tissue attached at the margin of the cavity by the glenoid labrum 62. In the case of shoulder dislocation, a Bankart lesion 61 results where the labrum 62 is torn from the anterior rim 67 and inferior rim 68.

For arthroscopic viewing of the affected area 90, a generally downward-directed portal is opened just anterior to the supraspinatus tendon for a conventional cannula, for example, an Arthrex 8.2 clear threaded cannula. Another anterior portal is opened for a second cannula passing just above the upper border of the subscapularis tendon, lateral to the middle glenohumeral ligament. The second cannula provides access to the area of the lesion for conventional instruments, such as a tissue grasper. A posterior portal is opened for a generally forward-directed cannula 65 at a location just inferior to the postero-lateral corner of the acromion. The forwarded-directed cannula 65 provides access to the affected area by the offset drill guide 100 of the present invention.

An arthroscopic elevator 66 (FIG. 3) may be used to free any adhesions between the glenoid labrum 62 and the glenoid in preparation for anatomic repair of the fibrous cartilage, and to allow the glenoid labrum 62 and the glenoid capsule to "float" easily. The scapular neck and rim may be also slightly roughened with a burr or rasp to retain bone stock.

Figure 4:
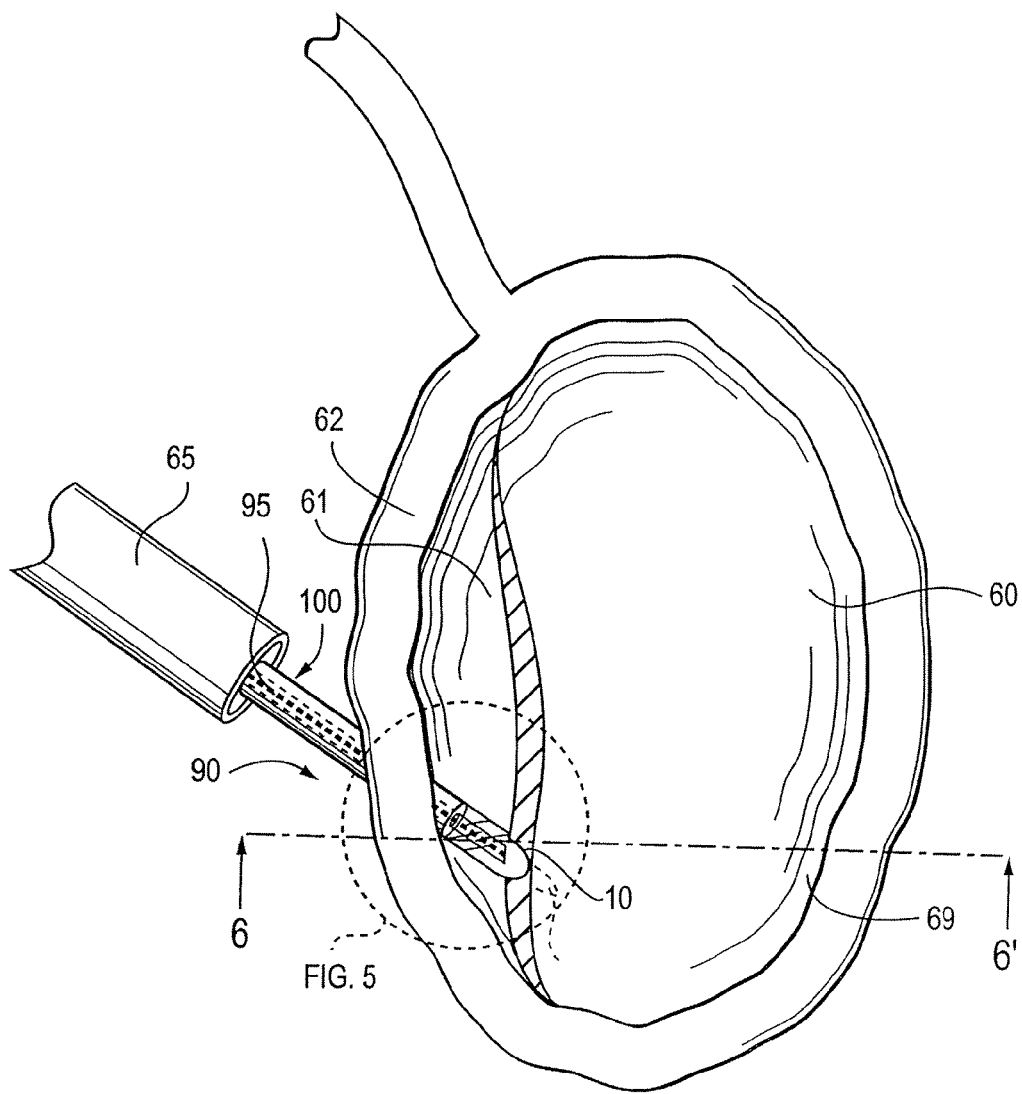
FIG. 4 illustrates a method step of straddling the glenoid rim with the offset drill guide of the present invention.
Figure 5:
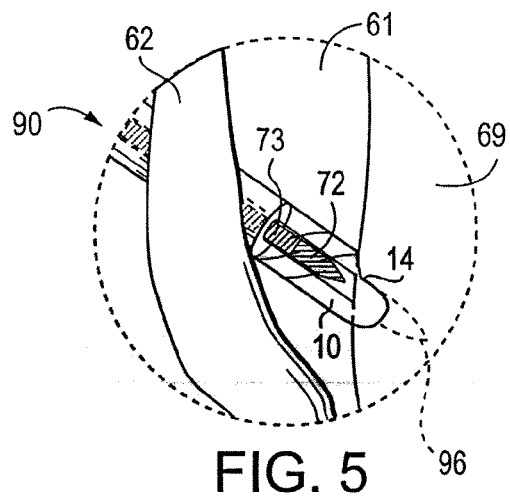
FIG. 5 illustrates a suture anchor and driver within the offset drill guide of the present invention.

Referring to FIGS. 4-5, the offset drill guide 100 is held in one hand using handle 80 (not shown in FIG. 4) and is inserted through cannula 65 into the proximity of the surgical site, approaching the Bankart lesion 61 to be repaired with concave clear tip 10. Once inserted, the offset drill guide 100 is seated at approximately 5:00 or 5:30 position relative to the right shoulder, for example.

Figure 6:
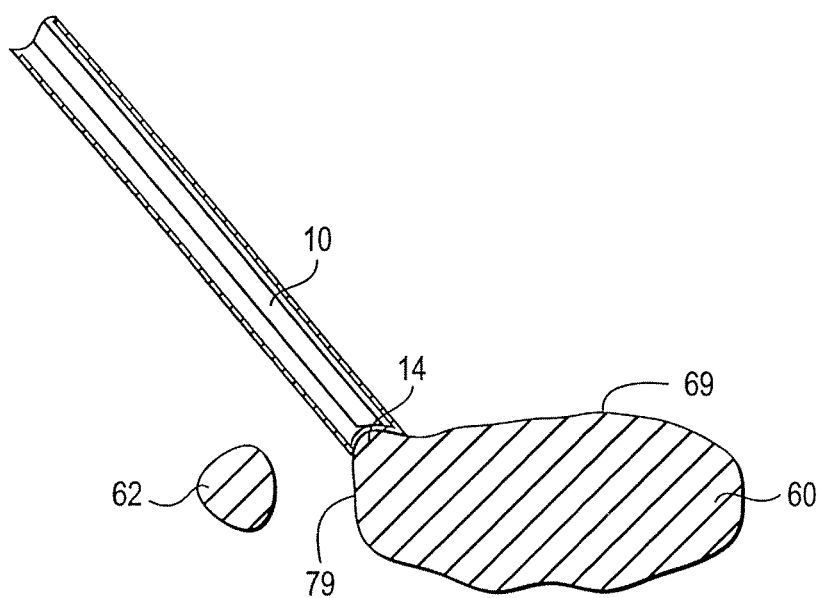
FIG. 6 illustrates a cross-sectional view of the structure of FIG. 4 taken along line 6-6'.

As illustrated in more detail in FIGS. 5 and 6, the offset drill guide 100 is placed so that the concave clear tip 10 is positioned with its concave-shaped surface 13 in direct and precise alignment with the convex-shaped bony surface of the glenoid rim. The preferably concave surface 13 (FIG. 2) of the instrument 100 through which its offset shaft opens is placed against and engages the convex rim of the glenoid, helping to stabilize the instrument. Thus, the configuration of the concave clear tip 10 is designed to engage and match the generally convex-curve articulating face of the glenoid. In this manner, by precisely aligning the offset drill guide with the glenoid face, uniform pressure is exerted over the entire contact region of the glenoid rim. If the distal surface of the tip of the instrument were cylindrical, as is the case with other shafts, then only localized pressure would be applied in particular areas of the articular cartilage and rim, which could damage the cartilage and dislodge the instrument.

In addition, by providing the offset drill guide with a shaft which extends obliquely relative to the guide center line and is offset from the guide center line by about 1 to 3 mm, more preferably of about 1.5 mm, the offset shaft allows the placement of a pilot or blind hole for an anchoring device, for example a suture anchor, slightly onto glenoid face 69 (FIG. 6) at a precise location and with minimal amount of bone removed. The pilot or blind hole for the anchoring device is also located on the face 69 of the glenoid 60 and as high as possible from articulating surface 79 of the glenoid 60, to allow better fixation of the damaged labrum 62 on the face of the glenoid. Compare FIGS. 7A and 7B (showing a drill guide 200 without offset and corresponding tissue placement) with FIGS. 8A and 8B (showing the offset drill guide 100 of the present invention and corresponding corrected tissue placement higher on the glenoid rim). Further, the concave tip 10 of the cannulated offset drill guide 100 is clear to allow the surgeon to visualize the drill and the insertion of the suture anchor. The concave clear tip has smooth edges to prevent damage to adjacent bone and tissue, and to prevent damage to the rubber dam attached to the cannula through which the offset drill guide is inserted.

Once the offset drill guide 100 has been positioned in direct and precise alignment with the glenoid rim, a drill pin 95 (FIG. 4) is inserted through offset drill guide 100 and a 2.4 drill hole 96 (FIG. 4) is created to the drill stop and into the glenoid face 69. Drill pin 95 is then removed and a tissue repair device, for example, an Arthrex Bio-Suture Tak (3 mm) or a suture anchor 72 (FIG. 5) and a suture anchor driver 73 (FIG. 5) pre-threaded with suture is inserted through the cannula of offset guide 100. The anchor is advanced into the 2.4 drill hole 96 to a laser line on the inserter, matching the back of guide.

The sutures are then brought out through the superior cannula and secured with a hemostat. The labrum is subsequently captured along with a "tuck" of capsule at the 5:30 position using a 90 degree suture passer, such as Arthrex pigtail passer. This suture is then used as a shuttle to pass a single limb of the suture from the suture anchor through the labrum. A sliding knot, such as the self-locking Roeder knot or the Harryman knot, is then tied with the suture through the labrum as the "post" limb. The knot is subsequently secured with additional half hitches switching the post and alternating throws.

The above-described process is repeated at approximately the 4:00 and 2:30 position. Alternatively, the suture limb can be placed in the labrum first using the same shuttle technique. The suture can then be loaded into the Bio-Suture Tak with the slotted plication driver prior to implantation of the suture anchor. With the above-described alternative technique, the offset drill guide is used to drill only a pilot hole and it must be removed to allow for a free-hand insertion of the suture anchor.

As noted above, by providing the offset drill guide 100 with a shaft which is offset from the guide center line 15 by about 1 to 3 mm, more preferably of about 1.5 mm, the offset shaft allows the placement of a pilot or blind hole for an anchoring device slightly onto glenoid face 69 and at a precise location and with minimal amount of bone removed. The pilot or blind hole for the anchoring device is also located on the face 69 of the glenoid 60 and as high as possible from articulating surface 79 of the glenoid 60, to allow better fixation of the damaged labrum on the face of the glenoid. This aspect of the invention is exemplified in FIGS. 7A-7B and 8A-8B, which illustrate a comparison of the location of the pilot hole formed with a drill guide without offset vis-à-vis the location of a pilot hole formed with a drill guide with offset of the present invention.

Figure 7A:
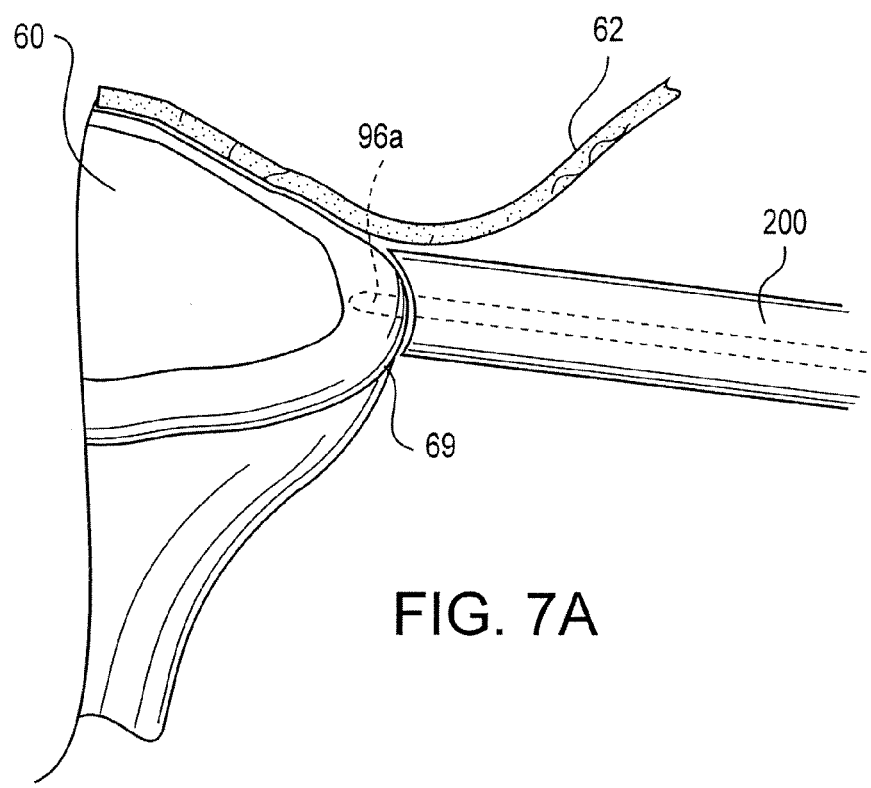
FIG. 7A illustrates a perspective view looking medially and superiorly of the joint illustrating a drill guide without any offset and, in FIG. 7B, the corresponding location of tissue attachment to the glenoid.
Figure 7B:
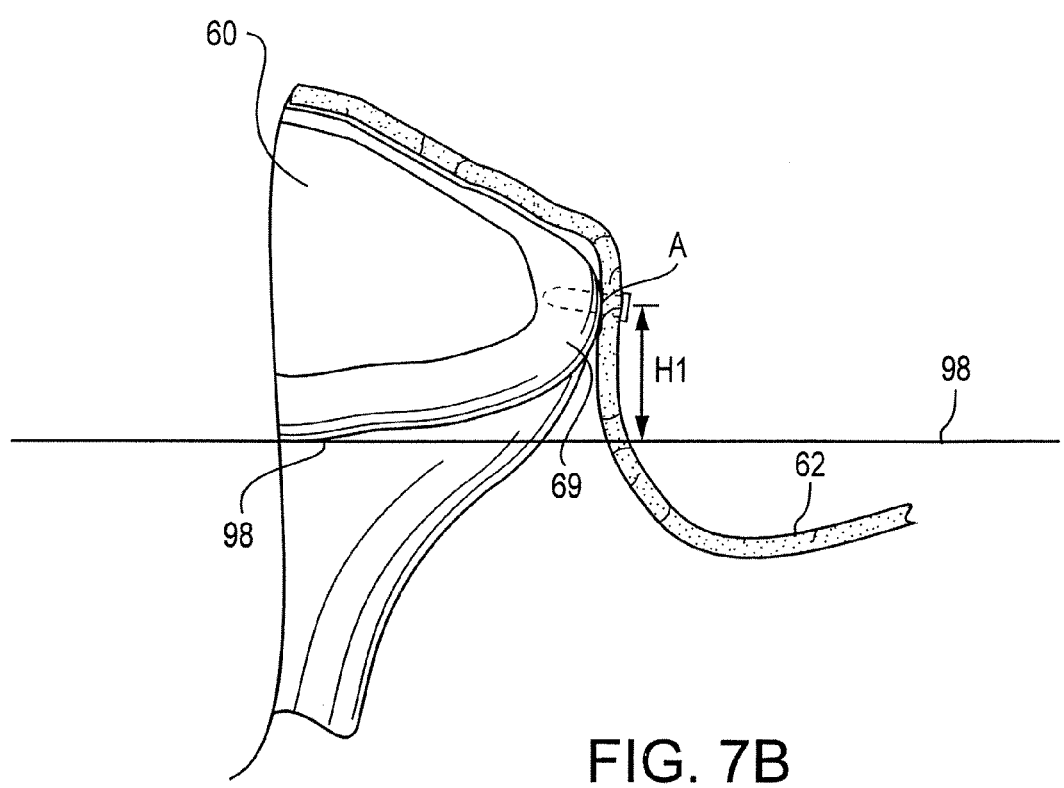
Figure 8A:
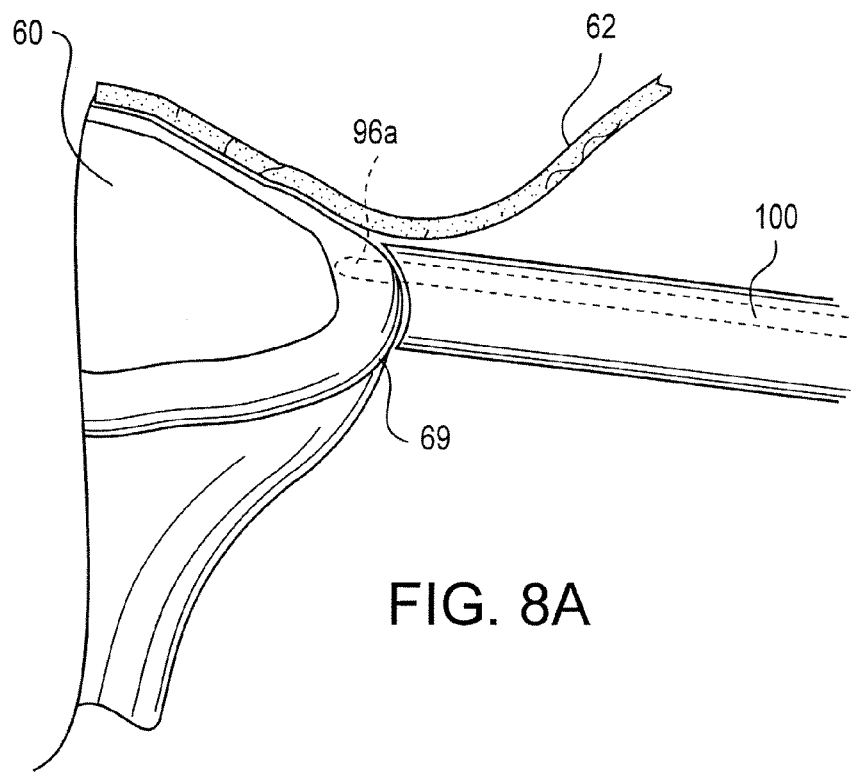
FIG. 8A illustrates a perspective view like FIG. 7A but with the offset drill guide of the present invention, and Figure B shows the corresponding corrected tissue placement.
Figure 8B:
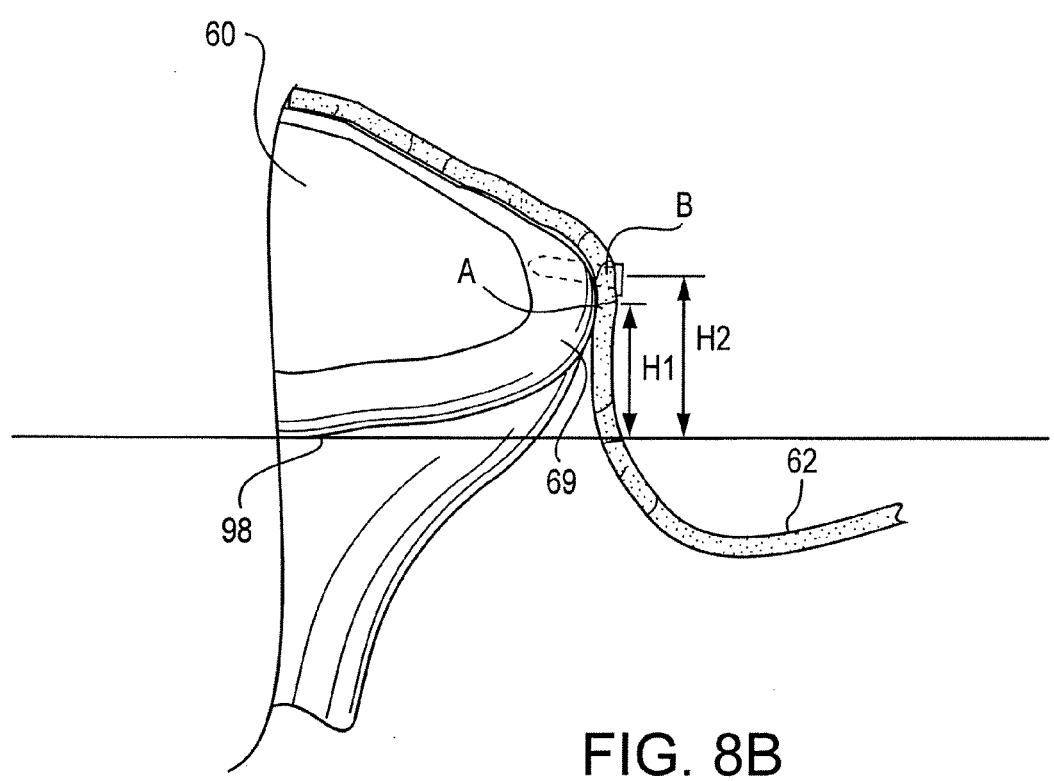

Specifically, FIG. 7A illustrates the position of a drill guide 200 without offset and the location of corresponding pilot hole 96a to allow tissue placement of glenoid labrum 62 at a first location A (FIG. 7B) on the glenoid rim. As shown in FIG. 7B, first location A is provided on the glenoid face 69 at a height $H_1$ relative to most inferior surface line 98 (FIG. 7B) of the glenoid face 69. FIGS. 8A and 8B illustrate the offset drill guide 100 of the present invention and the location of pilot hole 96 for allowing corresponding corrected tissue placement of glenoid labrum 62 at a second location B (FIG. 8B). As illustrated in FIG. 8B, the second location B is provided on the glenoid face 69 at a height $H_2$ relative to most inferior surface line 98 (FIG. 7B) of the glenoid face 69. Height $H_2$ of the second location B for the placement of glenoid labrum 62 is greater than the height $H_1$ by at least distance "D" of about 2 to 3 mm, more preferably of about 2.5 mm. Thus, the second location B for the placement of the glenoid labrum 62 is located higher on the glenoid rim relative to the first location A.

Although the embodiments of the present invention have been described above with reference to a Bankart repair, it must be understood that the invention has equal applicability to other arthroscopic surgeries that require precise attachment of damaged tissue to bone or cartilage. Thus, the present invention also contemplates repairing a detachment of any connective tissue to bone or cartilage by employing the cannulated offset drill guide of the present invention.

In addition, although the embodiments of the present invention have been described above with reference to an offset guide, as discussed previously, the clear tip 10 may be employed in a co-linear drill guide having a cannulation which is not offset from the center line of the body.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A drill guide, comprising:
    a handle;
    a cannulated body having a proximal end and a distal end, the distal end terminating in a cannulated tip terminating in a most distal surface which is curved and concave, the most distal curved and concave surface being configured for engaging and matching a generally convex-curve articulating face of a glenoid; and
    a center line extending through the center of the cannulated body and the handle;
    wherein the cannulated tip with the most distal curved concave surface is offset from the center line of the cannulated body by about 1 to 3 mm, and
    wherein the cannulated tip allows a drill pin to be inserted and passed through it to form a drill hole on the articulating face of the glenoid.

2. The drill guide of claim 1, wherein the cannulated tip is offset from the center line of the cannulated body by about 1.5 mm.

3. The drill guide of claim 1, wherein the concave distal surface of the tip further comprises a first inclined surface and an adjacent second inclined surface.

4. The drill guide of claim 3, wherein the first inclined surface and the second inclined surface form an angle relative to the center line of the cannulated elongated body.

5. The drill guide of claim 4, wherein the angle is greater than about 90 degrees.

6. The drill guide of claim 4, wherein the angle is of about 110 to about 130 degrees.

7. The drill guide of claim 1, wherein the handle is affixed to the proximal end of the cannulated body.

8. A drill guide comprising:
    a cannulated elongated body having a proximal end, a distal end and a center line extending through the center of the cannulated elongated body; and
    a clear tip having a most distal surface with a concave configuration for engaging and matching a generally convex-curve articulating face of a glenoid, the clear tip being located at the most distal end of the cannulated elongated body, the clear tip with the most distal surface being offset from the center line of the cannulated elongated body, the clear tip being cannulated to allow a drill pin to be inserted and passed through, to form a drill hole on the articulating face of the glenoid.

9. The drill guide of claim 8, wherein the tip is offset from the center line of the elongated body by a predetermined distance of about 1 to 3 mm.

10. The drill guide of claim 9, wherein the predetermined distance is of about 1.5 mm.

11. The drill guide of claim 8, wherein the distal concave surface further comprises a first inclined surface and a second inclined surface, the first inclined surface and the second inclined surface forming an angle greater than about 90 degrees relative to the center line of the cannulated elongated body.

12. The drill guide of claim 11, wherein the angle is of about 110 to about 130 degrees.

13. The drill guide of claim 8, further comprising a handle affixed to the proximal end of the cannulated elongated body.

* * * * *